(12) United States Patent
Filmus et al.

(10) Patent No.: US 7,883,853 B2
(45) Date of Patent: Feb. 8, 2011

(54) DIAGNOSIS OF HEPATOCELLULAR CARCINOMA

(75) Inventors: Jorge Filmus, Toronto (CA); Mariana Capurro, Toronto (CA)

(73) Assignee: Sunnybrook Health Sciences Centre, Toronto, Ontario (CA)

( * ) Notice: Subject to any disclaimer, the term of this patent is extended or adjusted under 35 U.S.C. 154(b) by 6 days.

(21) Appl. No.: 10/514,294

(22) PCT Filed: May 22, 2003

(86) PCT No.: PCT/CA03/00752

§ 371 (c)(1),
(2), (4) Date: May 23, 2005

(87) PCT Pub. No.: WO03/100429

PCT Pub. Date: Dec. 4, 2003

(65) Prior Publication Data

US 2005/0233392 A1    Oct. 20, 2005

Related U.S. Application Data

(60) Provisional application No. 60/382,340, filed on May 23, 2002.

(51) Int. Cl.
*G01N 33/53* (2006.01)
(52) U.S. Cl. ...................... 435/7.1; 435/7.72
(58) Field of Classification Search .................. None
See application file for complete search history.

(56) References Cited

U.S. PATENT DOCUMENTS 5,171,850 A * 12/1992 Filmus et al. .............. 536/23.5
5,418,147 A    5/1995 Huang et al.

FOREIGN PATENT DOCUMENTS

| JP | 03043078 | 2/1991 |
| WO | WO 99/37764 | 7/1999 |
| WO | WO 00/23109 | 4/2000 |
| WO | WO 03/000883 | 1/2003 |

OTHER PUBLICATIONS

Toretsky (2001, J. Pediatr. Hematol. Oncol. 23(8):496-9) (abstract only).*
(Nakatsura et al., 2005, Biodrugs 19(2):71-77) (abstract only).*
Zhu (2001, Gut 48:558-564).*
Filmus (2001, Glycobiology 11:19R-23R).*
Lage et al. (1997, Gene 188:151-156).*
(http://www.ihop-net.org/UniPub/iHOP/gs/88647.html; as downloaded Sep. 26, 2007).*
Capurro et al., (2002), Proceedings of the American Association for Cancer Research Annual Meeting, 2002, v. 43, p. 219, Abstract No. 1097.
Xu et al., (1998), Journal of Clinical Endocrinology and Metabolism, v. 83, pp. 437 to 442.
Gonzalez et al., (1998), Journal of Cell Biology, v. 141, pp. 1407 to 1414.
Hemming et al., (1995), J. Biol. Chem., v. 270, pp. 5360 to 5366.
Guanghi et al., (2001), Chinese Journal of Anatomy, v. 24, p. 502 (English language Abstract).
Di Bisceglie, "Hepatitis C and Hepatocellular Carcinoma" (1995), Semin.Liver Dis., v. 15, pp. 64-69.
Capurro, et al., "Overexpression of Glypican-3 in human hepatocellular carcinomas determined by immunohistochemistry using a monoclonal antibody" (2002), Proc. Amer. Assoc. for Cancer Research, v. 43, pp. 219, A1097.
Capurro, et al., "A Novel Serum and Histochemical Marker for Hepatocellular Carcinoma" (2003), Gastroenterology, v. 125, pp. 89-97.
Collier, et al. "Screening for Hepatocellular Carcinoma" (1998), Hepatalogy, v. 27, pp. 273-278.
Collier, et al., "Significance of Elevated Alpha-Fetoprotein in the Absence of Hepatocellular Carcinoma in Chronic Viral Hepatitis" (1998), Viral Hepatitis Reviews, v. 4, pp. 31-41.
Deuffic, et al. "Trends in primary liver cancer" (1998), Lancet, v. 351, pp. 214-215.
Duenas Gonzales, et al., "OCI-5/GPC3, a Glypican Encoded by a Gene That Is Mutated in the Simpson-Golabi-Behmel Overgrowth Syndrome, Induces Apoptosis in a Cell Line-specific Manner" (1998), J.Cell.Biol., v. 141, pp. 1407-1414.
El-Serag, et al., "Rising Incidence of Hepatocellular Carcinoma in the United States" (1999), N. Engl.J.Med., v. 340, pp. 745-750.
Hasan, et al., "Hepatitis C-associated Hepatocellular Carcinoma" (1990), Hepatalogy, v. 12, pp. 589-591.
Hsu, et al., "Cloning and Expression of a Developmentally Regulated Transcript MXR7 in Hepatocellular Carcinoma: Biological Significance and Temporospatial Distribution1" (1997), Cancer Res., v. 57, pp. 5179-5184.
Kleeff, et al., "Glypican-3 is a Potential Tumor Marker for Hepatocellular Carcinoma" (2000), Gastroenterology, v. 118, pp. A261.
Levy, et al., "Resection of Hepatocellular Carcinoma Without Preoperative Tumor Biopsy" (2001), Ann.Surg., v. 234, pp. 206-209.
Nakatsura, et al., "Glypican-3, overexpressed specifically in human hepatocellular carcinoma, is a novel tumor marker" (2003), Biochem, Biophys. Res. Comm., v. 306, pp. 16-25.
Nalpas, et al., "Hepatocellular Carcinoma in Alcoholics" (1995), Alcohol, v. 12, pp. 117-120.
Nomura, et al., "Serum Des-Gamma-Carboxy Prothrombin Levels Determined by a New Generation of Sensitive Immunoassays in Patients With Small-Sized Hepatocellular Carcinoma" (1999), Am.J. Gastroenterol., v. 94, pp. 650-654.
Parkin, et al., "Global Cancer Statistics" (1999), CA. Cancer J. Clin., v. 49, pp. 33-64.

(Continued)

*Primary Examiner*—Anne M. Gussow
(74) *Attorney, Agent, or Firm*—Dinsmore & Shohl LLP

(57) ABSTRACT

A method is provided for screening a subject for hepatocellular carcinoma by determining the level of glypican-3 (GPC3) in a body fluid sample from the subject. A further method is provided for diagnosing hepatocellular carcinoma by detecting GPC3 in a liver tissue sample. Also provided are antibodies which bind specifically to GPC3.

16 Claims, 5 Drawing Sheets

OTHER PUBLICATIONS

Rustgi, "Epidemiology of Hepatocellular Carcinoma" (1987), Gastroenterol.Clin.North Am., v. 16, pp. 545-551.

Schiff, "Hepatitis C and Alcohol" (1997), Hepatology, v.26, pp. 39S-42S.

Seow, et al., "Hepatocellular carcinoma: From bedside to proteomics" (2001), Proteomics, v. 1, pp. 1249-1263.

Sherman, M., "Alphafetoprotein: an obituary" (2001), J.Hepatol., v. 34, pp. 603-605.

Sung, et al., "Glypican-3 is overexpressed in human hepatocellular carcinoma" (2003), Cancer Sci, v. 94, pp. 259-262.

Taketa, K., "alpha-Fetoprotein: Reevaluation in Hepatology" (1990), Hepatology, v. 12, pp. 1420-1432.

Thorgeirsson, et al., "Molecular pathogenesis of human hepatocellular carcinoma" (2002), Nature Genet., v. 31, pp. 339-346.

Trevisani, et al., "Serum alpha-fetoprotein for diagnosis of hepatocellular carcinoma in patients with chronic liver disease: Influence of HBsAg and anti-HCV status" (2001), J.Hepatol., v. 34, pp. 570-575.

Yuki, et al., "Growth and Spread of Hepatocellular Carcinoma" (1990), Cancer, v. 66, pp. 2174-2179.

Yu, "Primary prevention of hepatocellular carcinoma" (1995), J. Gastroenterol,Hepatol., v. 10, pp. 674-682.

Zou, et al. "Prediction of hepatitis C burden in Canada" (2000), Can. J. Gastroenterol., v. 14, pp. 575-580.

Zhu, et al., "Enhanced glypican-3 expression differentiates the majority of hepatocellular carcinomas from benign hepatic disorders"(2001), Gut, 48, pp. 558-564.

Proc. Annu. Meet. Am. Assoc. Cancer Res, 2002, vol. 43, p. 219 #1097.

Hey-Chi "Cloning and Expression of a Developmentally Regulated Transcript MXR7 to Hepatocellular Carcinoma: Biological Significance and Temporospatial Distribution", Cancer Res., 1997, Vo. 57, No. 22, pp. 5179-5184.

Xiang et al., "Glypican-3 expression is silenced in human breast cancer" Short Reports, 2001 Nature Publishing Group, pp. 7408-7412, Aug. 2001.

Veugelers et al., "Mutational analysis of the GPC3/GPC4 glypican gene cluster on Xq26 in patients with Simpson-Golapi-Behmel syndrome: identification of loss-of-function mutations in the GPC3 gene", Human Molecular Genetics, vol. 9., No. 9, pp. 1321-1328, Mar. 21, 2000.

Lapunzina et al., "A patient with Simpson-Golabi-Behmel syndrome and hepatocellular carcinoma" F Med Genet, 35: pp. 153-156, Aug. 29, 1997.

Powell et al., "Oligonucleotide Microarray Analysis of Lung Adenocarcinoma in Smokers and Nonsmokers Identifies GPC3 as a Potential Lung Tumor Suppressor", American College of Chest Physicians, Chest 2002; 121; 6S-7S.

Du X. et al., Down-Regulation of Glycosylphosphatidylinositol-Specific Phospholipase D Induced by Lipopolysaccharide and Oxidative Stress in the Murine Monocyte-Macrophage Cell Line RAW 264.7, Infection and Immunity, vol. 69, No. 5, May 2001 pp. 3214-3223.

Low M.G., Degradation of glycosyl-phosphatidylinositol anchors by specific phospholipases, Molecular and Cell Biology of Membrane Proteins: glycolipid anchors of cell-surface proteins, A.J. Turner (ed.), Ellis Horwood, New York, Chapter 2, 1990 pp. 35-63.

Ishihara M. et al., Involvement of Phosphatidylinositol and Insulin in the Coordinate Regulation of Proteoheparan Sulfate Metabolism and Hepatocyte Growth, The Journal of Biological Chemistry, vol. 262, No. 10, Issue of Apr. 5, 1987 pp. 4708-4716.

Hoof V.O.V. et al., How do plasma membranes reach the circulation? Clinica Chimics Acta 266 (1997) pp. 23-31.

Hari T., Subcellular distribution of glycosylphosphatidylinositol-specific phospholipase D in rat liver, Biochem. J. 320 (1996) pp. 315-319.

Song H.H. et al., The role of glypicans in mammalian development, Biochimica et Biophysics Acta 1573 (2002) pp. 241-246.

Clark P.M.S. et al., Immunoassays, Clinical Aspects of Immunology, Published by Blackwell Scientific Publications, Fifth Edition, vol. 2, Chapter 44 (1993) pp. 829-843.

Rowhani A., Use of F(ab')2 Antibody Fragment in ELISA for Detection of Grapevine Viruses, Am. J. Enol. Vitic., vol. 43, No. 1 (1992) pp. 38-40.

Notice of Opposition dated Dec. 18, 2009 pertaining to European Patent No. 1 506 406/European Patent Application No. 03724724.4.

Vessey, CJ et al.; Genetic disorders associated with cancer predisposition and genomic instability; Prog Nucleic Acid Res Mol Biol.; 1999; 189-221; 63.

* cited by examiner

DIAGNOSIS OF HEPATOCELLULAR CARCINOMA

RELATED APPLICATIONS

This application is a 371 of PCT/CA03/00752 filed May 22, 2003 and claims benefit under 35 U.S.C. §119 of U.S. Application Ser. No. 60/382,340 filed May 23, 2002.

FIELD OF THE INVENTION

The invention relates to the diagnosis of hepatocellular carcinoma. In particular, the invention relates to antibodies and methods for determining the level of glypican-3 as a marker for hepatocellular carcinoma.

BACKGROUND OF THE INVENTION

Throughout this application, various references are cited to describe more fully the state of the art to which this invention pertains. The disclosures of these references are hereby incorporated by reference into the present disclosure.

Hepatocellular carcinoma (HCC) is the most common solid-organ tumor in the world, being responsible for more than 1 million deaths annually (Parkin, et al., (1999) C A. Cancer J. Clin., 49:33-64, and Okuda, et al., (1993), Neoplasms of the Liver in Diseases of the Liver, 7th edition 1236).

The incidence of HCC is increasing in most Western countries (Deuffic, et al., (1998), Lancet 351:214-215). Although good epidemiological studies are not available, data from Health Canada indicate that the death rate from HCC in men has nearly doubled over the last 15 years. The demographics of patients with viral hepatitis suggest that the incidence will double again in the next 10 years (Zou, et al., (2000), Can. J. Gastroenterol., 14:575-580).

HCC is usually asymptomatic at early stages and has a great propensity for intravascular or intrabiliary invasion, even when the primary tumor is small (Fong, et al., (2001), Cancer of the Liver and Biliary Tree. in Cancer: Principles & Practice of Oncology, 6th Edition, 1162-1199). As a result, HCC is generally at an advanced stage when discovered. Historically, only 10-20% of primary HCCs are found to be resectable at the time of diagnosis (Fong, et al., (2001), Cancer of the Liver and Biliary Tree in Cancer: Principles & Practice of Oncology, 1162-1199). More recently, with the advent of HCC screening programs, the proportion of potentially curable tumors is increasing, although most patients still have incurable disease at the time of diagnosis.

HCC is associated with chronic liver injury, primarily chronic viral hepatitis and alcoholic liver disease (Rustgi, (1987), Gastroenterol. Clin. North Am., 16: 545-551). The highest incidence of HCC is found in areas were hepatitis B virus (HBV), and hepatitis C virus (HCV) are endemic. In the case of HBV, it has been demonstrated that the relative risk of developing HCC is 50- to 100-fold greater in individuals with evidence of chronic infection than in non-infected individuals (Beasley, et al., (1994), Epidemiology of hepatocellular carcinoma in Viral hepatitis and liver disease, 209). Unlike other causes of HCC, chronic hepatitis B cirrhosis is not a necessary precondition for the development of HCC. There are no estimates of relative risk with chronic HCV, but the incidence of HCC in cirrhotic carriers of HCV may be as high as 5% per year, compared to 0.5% for HBV carriers (Di Bisceglie, (1995), Semin. Liver Dis., 15:64-69). Persistent HCV infection is the cause of 70% of the cases of HCC in Japan, and the most likely reason for the rising incidence of HCC in North America is the increased spread of HCV infection in the population (Hasan, et al., (1990), Hepatology, 12:589-591 and El-Serag, et al., (1999), N. Engl. J. Med., 340:745-750).

Several chemicals have been linked to the development of HCC. The most important of them is ethanol, and alcohol abuse has been linked to HCC (Schiff, (1997), Hepatology, 26:39S-42S and Nalpas, et al., (1995), Alcohol, 12:17-120). Ethanol is thought to produce HCC through the generation of hepatic cirrhosis or as a co-carcinogen with other agents such as HBV and HCV. Aflatoxins produced by several fungi have also been linked to HCC (Yu, (1995), J. Gastroenterol. Hepatol., 10:674-682). These fungi tend to grow on grains, peanuts, and other food products, and are the most frequent cause of food spoilage.

The diagnosis of HCC is relatively straightforward in patients with a space-occupying lesion on ultrasonography or computed tomography (CT), and serum alphafetoprotein (AFP) of more than 500 ng/ml (Fong, et al., (2001), in Cancer of the Liver and Biliary Tree in Cancer: Principles & Practice of Oncology, 6th Edition, 1162-1199). In general, however, by the time these conditions are met, the HCC is untreatable, since very frequently the AFP is not diagnostically elevated.

Diagnosis by imaging of small lesions is relatively inaccurate, whether by ultrasonography, CT scanning or MRI (Fong, et al., (2001), in Cancer of the Liver and Biliary Tree in Cancer: Principles & Practice of Oncology, 6th Edition, 1162-1199); and Murakami, et al., (1995), Detectability of hypervascular hepatocellular carcinoma by arterial phase images of MR and spiral CT. Acta Radiol., 36: 372-376). In particular, the two lesions which may mimic HCC radiologically are cirrhotic nodules and dysplastic nodules. Liver biopsy of small lesions is also insufficiently sensitive or specific (Levy, et al., (2001), Ann. Surg., 234:206-209). Even with a needle biopsy, a well-differentiated cancer may be difficult to distinguish from benign lesions due to the limited amount of material usually obtained by this procedure (Fong, et al., (2001), in Cancer of the Liver and Biliary Tree in Cancer: Principles & Practice of Oncology 6th Edition, 1162-1199). Thus despite the advances in imaging technology, there is still a need for a suitable molecular marker to distinguish HCC from benign liver lesions in difficult cases.

The size of a tumor is a significant risk factor for intrahepatic spread and metastasis of HCC (Yuki, et al., (1990), Cancer, 66:2174-2179). In addition, many more treatment options are available for patients with small tumors. Symptomatic tumors are generally large, and beyond therapeutic intervention. Another situation where a sensitive and specific marker for HCC would be useful is in screening of patients at risk, such as chronic carriers of HBV and individuals with cirrhotic HCV. Although this screening is widely applied, there are as yet few data to suggest that it is effective in reducing disease (Collier, et al., (1998), Hepatology, 27:273-278). One of the reasons why screening has not been shown to be effective is that the serological test currently used, namely sequential AFP assays, has low sensitivity and specificity (Collier, et al., (1998), Viral Hepatitis Reviews, 4:31-41). Thus, improved test systems are needed to improve screening for HCC.

The only molecular marker that has been widely used for the screening and diagnosis of HCC is alphafetoprotein (AFP). This protein is synthesized in large quantities during embryonic development by the yolk sac and by the liver (Chan, et al., (1999), in Tumor Markers. in Tietz textbook of clinical chemistry, 3rd, 722-749, Taketa, K (1990), Hepatology, 12:1420-1432). AFP concentration decreases gradually after birth to <10 ng/ml in 12-18 months. AFP reappears in maternal serum during pregnancy. Increased circulating AFP has been associated with HCC, gastric carcinoma, lung cancer, pancreatic cancer, biliary tract cancer, and testicular carcinoma (Chan, et al., (1999), in Tumor Markers. in *Tietz textbook of clinical chemistry*, 3rd, 722-749).

If AFP levels of 20 ng/ml or higher are considered diagnostic, 60 to 80% of HCC cases are detected but, in the case of small tumors, sensitivity is significantly lower (40%) (Trevisani, et al., (2001), *J. Hepatol.*, 34:570-575). Another problem with the use of AFP as a marker for HCC is its lack of specificity; significant increases of AFP (20-200 ng/ml) are seen in a considerable number of patients with chronic liver diseases (Collier, et al., (1998), *Viral Hepatitis Reviews*, 4:31-41). It has been reported that 15-58% of patients with chronic hepatitis, and 11-47% with cirrhosis had increased serum AFP (Taketa, (1990), *Hepatology*, 12:1420-1432). It is, therefore, not uncommon that serum AFP levels in patients with HCC and cirrhosis overlap, which confounds the interpretation of the results of the AFP assay. Consequently, the usefulness of AFP measurement as a surveillance tool for patients at risk for HCC has been questioned (Sherman, (2001), *J. Hepatol.*, 34:603-605). It has been proposed, therefore, that the only circumstance in which the measurement of AFP is justified is for the confirmation of an initial diagnosis based on an imaging technique (Sherman, (2001), *J. Hepatol.*, 34:603-605).

In view of the unreliability of AFP levels, most screening regimens include ultrasonography, which is highly sensitive to liver masses. However, ultrasonography lacks specificity, and cannot reliably distinguish between HCC, cirrhotic nodule and dysplastic nodule when the lesions are smaller than about 2 cm.

In the last few years, several new potential markers for HCC have been investigated, but nothing clearly superior to AFP has been found (Seow, et al., (2001), *Proteomics*, 1:1249-1263). For example, des-gamma-carboxy prothrombin has been proposed as a potential marker. However, this molecule, like AFP, is not useful for the detection of small tumors (Nomura, et al., (1999), *Am. J. Gastroenterol.*, 94:650-654).

In 1997, Hsu et al., reported that, by performing differential mRNA display analysis of normal liver and HCC, they had identified a transcript that was upregulated in HCC (Hsu, et al., (1997), *Cancer Res.*, 57:5179-5184). This transcript, which they named MXR7, turned out to be Glypican-3 (GPC3). GPC3 is a heparan sulfate proteoglycan that is bound to the cell surface by a lipid tail (Duenas Gonzales, et al., (1998), *J. Cell. Biol.*, 141:1407-1414). Hsu et al. found that GPC3 mRNA was expressed in 143 out of 191 (74.8%) primary and recurrent HCCs, but in only 5 of 154 (3.2%) normal livers.

A second study found over-expression of GPC3 mRNA in 75% of HCC cases, but no over-expression was detected in focal nodular hyperplasia and cirrhotic liver (Zhu et al., (2001), Gut, 48, 558-564).

These studies analyzed only mRNA levels and it is known that mRNA levels do not always correlate with protein expression and secretion. In addition, only a limited number of liver proteins are normally secreted to the circulation.

While these results suggested that GPC3 mRNA analysis in liver tissue might be useful for the detection of HCC, this type of analysis is invasive, since it requires the isolation of tumor tissue. Furthermore, mRNA analysis is time-consuming and difficult to perform routinely.

There is therefore a need for a serum marker which can be used for screening (i.e. which will be positive in a high proportion of asymptomatic patients with small HCC's). In patients where an ultrasound has identified a small mass lesion, the test should also be able to reliably separate patients with HCC from those with non-malignant lesions.

In conclusion, there is still a need for better molecular markers for HCC, particularly for the surveillance of high risk populations, such as HCV patients with established cirrhosis. The search for such markers has been very difficult due to the high degree of heterogeneity that characterizes HCCs (Thorgeirsson, et al., (2002), *Nature Genet*, 31:339-346).

SUMMARY OF THE INVENTION

The inventors have found a new serum marker for HCC, glypican-3 (GPC3), which provides a basis for a new, rapid, convenient and non-invasive assay that offers improved specificity in the diagnosis of HCC.

In accordance with one embodiment of the present invention, there is provided a method for screening a subject for hepatocellular carcinoma (HCC) comprising:
    obtaining a body fluid sample from the subject; and
    determining the level of glypican-3 (GPC3) in the sample;
        wherein the presence of a detectable level of GPC3 in the sample is suggestive of HCC in the subject.

In accordance with another embodiment of the present invention, there is provided a substantially purified antibody or fragment thereof which binds specifically to GPC3 or to a fragment thereof.

In accordance with another embodiment of the present invention, there is provided a method for diagnosing HCC in a subject comprising:
    obtaining a liver tissue sample from the subject; and
    determining the presence of GPC3 in the tissue sample;
        wherein detection of GPC3 in the sample is indicative of HCC.

In accordance with another embodiment of the present invention, there is provided a method for detecting the presence of GPC3 in a sample, the method comprising:
    contacting a sample with an antibody or fragment thereof which binds specifically to GPC3 or to a fragment thereof to permit formation of an antibody-GPC3 complex, or antibody-GPC3 fragment complex; and
    detecting the antibody-GPC3 or antibody-GPC3 fragment complex.

In accordance with another embodiment of the present invention, there is provided a method for determining the level of GPC3 in a sample, comprising:
    contacting a sample with an antibody or fragment thereof which binds specifically to GPC3 or to a fragment thereof to permit formation of an antibody-GPC3 or antibody-GPC3 fragment complex; and
    determining the antibody-GPC3 or antibody-GPC3 fragment complex.

In accordance with another embodiment of the present invention, there is provided a kit for detecting or determining the level of GPC3 in a sample comprising:
    a substantially purified antibody or fragment thereof which binds specifically to GPC3 or to a fragment thereof.

BRIEF DESCRIPTION OF THE DRAWINGS

Preferred embodiments of the invention are described with respect to the drawings, wherein.

DETAILED DESCRIPTION OF THE INVENTION

Figure 1:
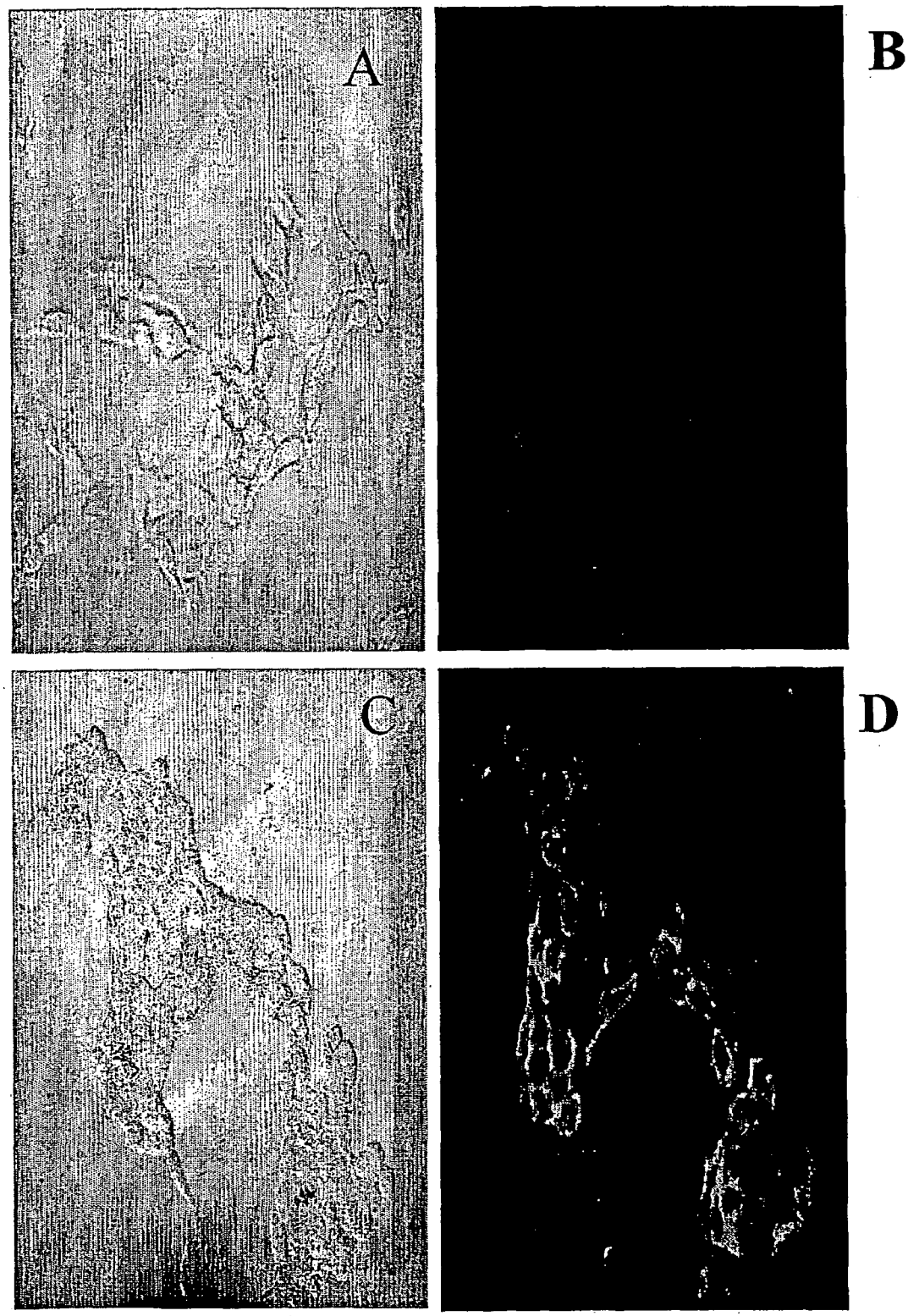
FIG. 1 shows photomicrographs of GPC3-transfected 293 cells (Panels C and D) and control cells transfected with vector only (Panels A and B), stained with anti-GPC3 monoclonal antibody 1G12. Panels A and C are phase contrast micrographs and Panels B and D are fluorescent micrographs.

The present invention provides a new method for screening a mammalian subject for hepatocellular carcinoma (HCC). The inventors have established that the cell surface proteoglycan GPC3 can be detected in the circulation, in the serum or plasma, of subjects with HCC, but does not occur at a detectable level, i.e. a level significantly above background, using a standard test of significance as described herein, in the serum or plasma of normal subjects. It has also been shown that little or no GPC3 can be detected in serum or plasma of subjects suffering from hepatitis or from hepatitis plus cirrhosis.

There is therefore provided a convenient, non-invasive method for screening a subject for HCC by determining GPC3 levels in a body fluid from the subject. Suitable body fluids for testing include serum, plasma and whole blood. Screening of serum or plasma is preferred.

GPC3 levels in a body fluid may be determined by any suitable method for measuring that protein. Immunological methods of determining GPC3 levels are highly convenient, and suitable types of methods will be well known to those in the art, and are further described herein.

For example, antibodies or antibody fragments which bind specifically to human GPC3 provide the basis for a variety of antibody-based assay methods for determining GPC3. HCC may be diagnosed by contacting a body fluid from the subject with an antibody or fragment which binds specifically to GPC3 under conditions permitting formation of an antibody-GPC3 complex and then detecting and/or determining the level of that complex. The amount of antibody-GPC3 complex correlates with the level of GPC3 in the sample.

The term "antibody", as used herein and if not otherwise specified, includes a polyclonal antibody, a monoclonal antibody, a chimeric antibody, a humanised antibody and a single chain antibody.

The term "antibody fragment" means a portion of an antibody that displays the specific binding of the parent antibody and includes Fab, F (ab')$_2$ and F$_v$ fragments.

As used herein, an antibody or antibody fragment is said to "bind specifically" to a target molecule if the antibody or antibody fragment recognises and binds the target molecule but does not substantially recognise and bind other molecules present in a sample containing target molecules.

Chimeric antibodies are antibodies which contain portions of antibodies from different species. For example, a chimeric antibody may have a human constant region and a variable region from another species. Chimeric antibodies may be produced by well known recombinant methods, as described in U.S. Pat. Nos. 5,354,847 and 5,500,362, and in the scientific literature (Couto et al., (1993), Hybridoma, 12:485-489).

Humanised antibodies are antibodies in which only the complementarity determining regions, which are responsible for antigen binding and specificity, are from a non-human source, while substantially all of the remainder of the antibody molecule is human. Humanised antibodies and their preparation are also well known in the art—see, for example, U.S. Pat. Nos. 5,225,539; 5,585,089; 5,693,761 and 5,693,762.

Single chain antibodies are polypeptide sequences that are capable of specifically binding a peptide or epitope, where the single chain antibody is derived from either the light or heavy chain of a monoclonal or polyclonal antibody. Single chain antibodies include polypeptides derived from humanised, chimeric or fully-human antibodies where the single chain antibody is derived from either the light or heavy chain thereof.

Antibodies

Polyclonal Antibodies

In order to prepare polyclonal antibodies, purified GPC3, human or non-human may be obtained.

GPC3 may be purified from, for example, human placenta by conventional methods, for example as described in Bonneh-Barkay et al., (1997), J. Biol. Chem., v. 272, pp. 12415-12421.

The purified protein may, if desired, be coupled to a carrier protein such as keyhole limpet hemocyanin, as is well known in the art, and is then mixed with Freund's adjuvant and injected into rabbits or other suitable laboratory animals.

Alternatively, all or a portion of the GPC3 protein can be synthesised recombinantly in a suitable host, such as a bacterium, by expression of an appropriate DNA sequence inserted into a suitable cloning vehicle. DNA encoding GPC3 may be cloned by previously described methods (Filmus et al., (1988), Molec. & Cell Biol., v. 8, pp. 4243-4249; Linsley et al., (1993), Ann. Rev. Immunol., v. 11, pp. 191-212; Peach et al., (1994), J. Exp. Med., v. 180, pp. 2049-2058). GPC3 or a portion thereof may be expressed as a fusion protein by similar methods.

Two widely used expression systems for producing recombinant fusion proteins in *E. coli* are gluthathione-S-transferase or maltose binding protein fusions using the pUR series of vectors and trpE fusions using the pATH vectors.

The expressed GPC3 protein can then be purified, for example using a glutathione column, coupled to a carrier protein if desired, and mixed with Freund's adjuvant (to help stimulate the antigenic response of the animal) and injected into rabbits or other appropriate laboratory animals. Following booster injections at weekly intervals, the rabbits or other laboratory animals are then bled and the sera isolated. The sera can be used directly or purified prior to use by various methods including affinity chromatography employing Protein A-Sepharse, antigen Sepharose or Anti-mouse-1 g-Sepharose.

Polyclonal antibodies may also be prepared using a fragment of GPC3 as antigen. Fragments of three or more consecutive amino acids from the GPC3 amino acid sequence may be used. A GPC3 fragment comprising the 70 amino acid carboxy-terminal amino acid sequence, or a portion thereof, is a preferred antigen. Fragments may be produced recombinantly, optionally as fusion proteins, as described herein. Such peptide antigens may be conjugated with keyhole limpet hemocyanin to improve antigenicity in vivo.

Monoclonal Antibodies

Monoclonal anti-GPC3 antibodies may also be produced by conventional methods after injecting into mice purified GPC3 or fragments thereof, optionally as fusion proteins, obtained as described above for preparation of polyclonal antibodies.

Briefly, the purified protein or peptide is injected into mice in Freund's adjuvant, for example for nine times over a three week period. The mice spleens are removed and resuspended in phosphate buffered saline (PBS). The spleen cells serve as a source of lymphocytes, some of which are producing antibody of the appropriate specificity. These are then fused with a permanently growing myeloma partner cell, and the products of the fusion, hybridomas, are plated into a number of tissue culture wells in the presence of a selective agent such as HAT. The wells are then screened by ELISA to identify those containing cells making antibody specific for GPC3. These cells are then plated and after a period of growth, these wells are again screened to identify antibody-producing cells. Several cloning procedures are carried out until over 90% of the wells contain single clones which are positive for antibody production. From this procedure, a stable line of clones which produce the antibody is established. The monoclonal antibody can then be purified by affinity chromatography using Protein A Sepharose or ion-exchange chromatography, as well as variants and combinations of these techniques.

In a further embodiment, antibody fragments are prepared, including but not restricted to $F(ab)_2$, $F(ab^1)_2$ and $F_v$ fragments or single chain components from GPC3-specific monoclonal antibodies. Such fragments may be generated using proteolytic cleavage of intact anti-GPC3 antibodies, for example as described in Lin et al., (1978), PNAS, 75(6); 2649-2653, or by genetic manipulation of genes encoding such fragments and fermentation of transfected production systems that are capable of secreting such anti-GPC3 antibody fragments.

Anti-GPC3 antibodies of an antigen affinity of at least $1\times10^8$ are preferred.

Various types of assay formats can be used to assay GPC3 in a sample. These include sandwich ELISA, radioimmunoassay, fluoroimmunoassay, dot-blot, dip-stick and Western Blot.

In a preferred embodiment, an antibody which binds specifically to GPC3 or to a fragment thereof and carries a detectable label is used and the resulting GPC3-antibody complex is determined by measuring the detectable label, thereby determining the level of GPC3 in the sample. Alternatively, a first antibody specific for GPC3 or a fragment thereof is employed, followed by a second antibody specific for the first antibody and carrying a label which may be a directly detectable label or may be a component of a signal-generating system. Such labeled antibodies and systems are well known in the art.

Detection and determination of the label or the signal generated by the signal-generating system, compared with suitable calibration standards, permits the determination of the GPC3-antibody complex present in the sample and hence of GPC3.

The second antibody carries a label which may be any suitable directly detectable label or a component of any suitable signal-generating system. Many examples of these are well known from the field of immunoassay.

Labeling of the second antibody with a detectable label or a component of a signal-generating system may be carried out by techniques well known in the art. Examples of labels that can be utilised to render an antibody detectable include radioisotopes, enzymes, fluorescent and chemiluminescent substances. For example, a radioactive element may be used as a directly detectable label; exemplary radioactive labels include the γ-emitters $^{124}I$, $^{125}I$, $^{128}I$, and $^{131}I$. A fluorescent label may also be used as a directly detectable label; for example, suitable fluorophores include coumarine, rare earth metal ions, chelates or chelate complexes, fluorescein, rhodamine and rhodamine derivatives.

Suitable labels also include metal complexes, stable free radicals, vesicles, liposomes, colloidal particles, latex particles, spin labels, biotin/avidin and their derivatives.

Enzyme-linked signal-generating systems may be used, including alkaline phosphatase, amylase, luciferase, catalase, beta-galactosidase, glucose oxidase, glucose-6-phosphate dehydrogenase, hexokinase, horseradish peroxidase, lactamase, urease and malate dehydrogenase. The activity of the enzyme can be detected by measuring absorbency, fluorescence or luminescence intensity after reacting the enzyme with an appropriate substrate. When enzymes are used as a label, the linkage between enzyme and antibody may be achieved by conventional methods such as glutaraldehyde, periodic acid and maleimide methods.

Solid matrices to act as solid supports suitable for immobilising an antibody include microtitre plates, such as those obtainable from Falcon Plastics, Oxnard, Calif., or, for example, regular ELISA microtitre plates (Immulon II, Dynax, Chantilly, Va.) and Streptavidin-coated ELISA microtitre plates (Reacti-Bind, Pierce, Rockford, Ill.), and microtitre strips, such as those obtainable from Dynatech, Alexandria, Va. The wells of the strips or the microtitre plates are made of clear plastic material, preferably polyvinyl chloride or polystyrene. Other solid matrices useful for antibody immobilisation include polystyrene tubes, sticks or paddles of any convenient size or polystyrene beads or polyacrylamide matrices.

Antibodies may be immobilised on a solid support by conventional methods which are well known in the art, for example as described in U.S. Pat. No. 5,352,583.

In accordance with a preferred embodiment of the invention, a sample of a body fluid is contacted with a first antibody which binds specifically to GPC3 to form a complex, the first antibody being immobilised on a solid support. Sufficient time is allowed to permit binding of the GPC3 of the sample to the immobilised antibody. The solid support is then washed and contacted with a second antibody which binds specifically to the first antibody and is labeled with a detectable label or has attached to it a signal-generating system. The label or generated signal bound to the solid support is determined, providing a measure of the complex present in the sample, and hence determining the level of GPC3 in the sample.

In accordance with a further embodiment, the sample is contacted simultaneously with the immobilised first antibody on the solid support and the labeled second antibody.

In a further embodiment, the second antibody may lack a label or signal-generating system component and the solid support-bound second antibody is determined by means of a third antibody bearing a detectable label or signal-generating system component, the third antibody binding selectively to the bound second antibody.

In accordance with a further embodiment, the sample is contacted, either simultaneously or stepwise, with a first antibody which binds specifically to GPC3 and to which is attached one member of a capture pair and with a labeled second antibody which binds to the first antibody. The resulting mixture is then contacted with a solid support on which is immobilised the other member of the capture pair. After allowing sufficient time for the labeled complex to bind to the solid support by interaction of the members of the capture pair, the solid support is washed and the amount of label bound to it is determined, to determine the level of GPC3 in the sample. Suitable capture pairs include biotin/streptavidin. Other suitable pairs are known to those in the art. The specificities of the antibodies may be reversed, the first antibody binding specifically to the complex and the labeled second antibody binding specifically to GPC3.

The screening method described herein appears to be highly specific for HCC, in that GPC3 was undetectable in samples from normal subjects and hepatitis sufferers, and was found at negligible levels in occasional hepatitis plus cirrhosis sufferers.

In trials using subjects with diagnosed HCC, from 53 to 55% of subjects had detectable serum GPC3 levels, ranging from 151 ng/ml to 2924 ng/ml.

When serum AFP was used as an HCC marker in the same patients, and 20 ng/ml was used as the threshold of abnormality, 59% of HCC patients were detected. If the threshold level of AFP indicative of disease is raised to 100 ng/ml, only 32% of HCC cases are detected. A threshold level of 20 ng/ml AFP, however, will include a number of false positives, since AFP levels greater than 20 ng/ml are seen in many chronic liver diseases other than HCC.

It has been found by the inventors that elevated levels of GPC3 in HCC patients was not well correlated with AFP levels (Table 4). The method of the invention therefore provides a useful additional tool for identifying HCC cases not detected by AFP screening. The method of the invention may be used alone or in addition to AFP screening by conventional methods to improve the ability to identify HCC at an early and treatable stage.

In a further embodiment of the invention, GPC3 and AFP screening may be used in combination to provide a test combining the specificity of screening for high levels of AFP with the improved sensitivity of GPC3 screening. For example, as seen from the data of Table 4, if AFP and GPC3 serum levels are determined and a threshold of 100 ng/ml AFP is used as the threshold of significance, 70% of HCC patients showed elevation of at least one of AFP and GPC3, as opposed to 32% if 100 ng/ml AFP is used alone as HCC marker, or 53% if GPC3 is used alone as marker. If both AFP and GPC3 are considered and a threshold value of 20 ng/ml AFP is used, 82% of patients showed elevation of at least one of AFP and GPC3.

The serological GPC3 assays of the invention are especially useful for further assessment of subjects showing clinical indications of a liver mass. The assays may also be used to screen populations at risk for HCC, for example chronic hepatitis B or C sufferers or carriers.

In a further embodiment, the invention provides an immunohistochemical method for diagnosing HCC by examining liver biopsy samples from subjects presenting with a liver mass. Liver tissue samples obtained by biopsy often show distorted morphology, making conventional histological diagnosis difficult. Tissue sections from such biopsies are stained with anti-GPC3 antibodies, as described in the examples herein, and detection of GPC3 in the sections is indicative that the biopsied mass is HCC. The anti-GP3 antibodies may themselves carry a detectable label, such as a fluorescent label, or the first anti-GPC3 antibody may be detected by a detectably labelled second antibody.

The present invention also provides antibodies which bind specifically to GPC-3. Antibodies which bind to the same epitopes as these antibodies are also encompassed within the invention. The antibodies may be of any immunoglobulin class including IgG, IgM, IgA, IgE and IgD and any subclass thereof.

In a further embodiment, the invention provides a kit comprising a substantially purified antibody or fragment thereof which binds specifically to GPC3 or to a fragment thereof.

In a further embodiment, the kit is for a standard two-antibody sandwich assay in which a first GPC3-specific antibody captures GPC3 present in the fluid sample and a second antibody detects the presence of the captured GPC3. The capture antibody is typically immobilized on a solid phase such as an ELISA plate, a nitrocellulose membrane, a bead or any other support known in the art. The detecting antibody is either directly labeled with a colorimetric or radioisotopic label or is itself detected by a secondary, labeled antibody specific for the isotype of the detecting antibody.

EXAMPLES

The examples are described for the purposes of illustration and are not intended to limit the scope of the invention.

Methods of chemistry, molecular biology, protein and peptide biochemistry and immunology referred to but not explicitly described in this disclosure and examples are reported in the scientific literature and are well known to those skilled in the art.

Methods

Patient tissues: Liver tissue samples were obtained from the Department of Pathology, Toronto General Hospital. All liver specimens were large blocks from surgically resected tumors and adjacent parenchyma. All tissue was fixed in 10% formalin and embedded in paraffin for routine histological examination.

Patient sera: Blood samples were obtained from 34 patients with HCC (see Table 3 for patient characteristics), 20 patients with hepatitis plus liver cirrhosis (12 with HCV and 8 with HBV), 18 patients with hepatitis (12 with HCV, 1 with HCV plus HIV, 1 with HCV plus Thalesemia, 1 coinfected with HCV and HBV and 3 with HBV) (Toronto General Hospital), and from 53 healthy blood donors (Sunnybrook and Women's College Health Sciences Centre, Toronto, Canada) under a signed consent from the patients. HCC was diagnosed histologically when liver biopsy was available or from clinical information following the guidelines of the European Association for Study of Liver Disease[20]. The serum was immediately separated by centrifugation and frozen at −20° C. Sera from patients that were diagnosed with non-malignant liver disease (hepatitis with liver cirrhosis and hepatitis) at the time of serum collection were only included in this study if there was no indication of malignant disease 6 months after such collection.

Cell lines: HCC cell lines HepG2, Hep3B and PLC-PRF-5 were cultured in minimum essential medium (MEM) with 10% fetal bovine serum (FBS) (Gibco BRL) and supplemented with MEM non-essential amino acid solution and sodium pyruvate (1 mM). The 293 cell line was cultured in DMEM and 10% FBS. All cell lines were obtained from the American Type Culture Collection, and were maintained at 37° C. in a humidified atmosphere with 5% $CO_2$. To collect conditioned media the cell lines were grown at high density overnight in the absence of serum. The collected media was concentrated using Centricon YM-10,000 filters (Millipore).

Transfection of GPC3: The 293 cell line was transfected with a hemaglutinin A (HA)-tagged-GPC3 cDNA[21] introduced into the pEF vector (or empty vector as control), and transfected cells selected with 800 μg/ml G418 (Gibco BRL). Cells expressing high levels of GPC3 were sorted by FACS after staining the G418-selected cells with an anti-HA 12CA5 Mab and a FITC-conjugated secondary antibody. Sorted cells were then expanded in tissue culture.

Production of anti-GPC3 mouse monoclonal antibodies: Balb/C female mice were immunized with a single i.p. injection of 50 μg of a His-tagged GPC3 fragment containing the last 70 amino acids of the core protein. The immunogen was emulsified with Titermax Gold (Cedarlane) adjuvant. After 21 days, the mice were boosted with 50 μg of the same immunogen in the absence of adjuvant. Two days later, blood samples were collected from the tail's vein, and the corresponding sera obtained. The anti-GPC3 titre in the serum samples was estimated by an ELISA using as negative control the pre-immunized serum from the same mice. Splenocytes obtained from the two mice with the highest titre were fused with SP2/0 Ag14 mouse myeloma cells (relation 6:1) in the presence of polyethylene glycol 4000 (Sigma) using standard procedures. The fused cells were placed into 96-wells plates and expanded in α-MEM, 10 mM Hepes, 50 μM 2-mercaptoethanol, 20% FBS supplemented with Nutridoma-CS (Roche) and hypoxanthine, aminopterin and thymidine (HAT supplement, Gibco BRL). To select for producing hybridomas the expanded clones were screened by ELISA, using 96-well plates loaded with 0.05 μg of GPC3 immunogen per well. The plates were blocked for 2 h with 1% bovine serum albumin (BSA) in phosphate-buffered saline (PBS), and conditioned media from each clone was added. The presence of anti-GPC3 antibodies bound to the antigen was detected using horseradish peroxidase-conjugated goat anti mouse-IgG and goat-anti mouse-IgM (StressGen) with O-phenylenediamine (Sigma) and hydrogen peroxide as substrates. The positive clones were then further expanded, and their ability to stain GPC3-transfected 293 cells was tested by immunofluorescence. The positive hybridomas, named 1G12 and 8H5, were re-cloned twice, and their isotype determined (IgG1, K) using Isostrip (Roche). Antibodies were purified from conditioned culture supernatants using protein A columns (Affi-Gel Protein A MAPS II kit, Bio-Rad).

Immunofluorescence: GPC3- or vector alone-293 transfected cells were seeded on poly-L-lysine treated slides, and fixed with 4% paraformaldehyde in PBS. After 1 hour incubation with anti-GPC3 Mab or normal mouse IgG (Santa Cruz Biotechnology)(15 μg/ml), the slides were washed 3 times with PBS, and the binding of the first antibody detected with FITC-conjugated sheep anti-mouse IgG F(ab')2 fragment (StressGen).

Western Blot analysis: Cells were lysed in RIPA buffer containing protease inhibitors (2 mM PMSF, 10 μg/ml leupeptin, 10 μg/ml aprotinin) for 30 min on ice. The protein samples were run on a 6% SDS-polyacrylamide gel and transferred to a PVDF membrane (Pall Corporation). The membranes were blocked in blocking buffer (10 mM Tris-HCl pH 8.0, 150 mM NaCl 0.1% Tween20, 5% non-fat dry milk) for 1 hour at room temperature, and then incubated with 1 μg/ml 1G12 or 12CA5 Mab overnight at 4° C. After incubation with horseradish peroxidase anti-mouse IgG secondary antibody for one hour, protein bands were detected using chemoluminescence ECL reagents (DuPont NEN).

Immunohistochemistry: Paraffin-embedded tissue sections were deparaffinized with xylene and rehydrated in a graded series of ethanol solutions. An antigen retrieval technique was then performed heating the slides in 10 mM citrate buffer pH 6 in a Kenmore microwave oven (2 min at power level 10, 1.5 min at power level 6 and 2.5 min at power level 9, and repeating these three steps twice). The slides were rinsed with distilled water, dehydrated in a graded series of ethanol, and dipped in 10% hydrogen peroxide in methanol for 10 minutes to block the endogenous peroxidase. The slides were rehydrated and immunostaining was performed using the anti-GPC3 Mab at 20 μg/ml (or normal mouse IgG and PBS as negative controls) according to the instructions of the Histostain-SP kit (Zymed Laboratories) and the TSATM Biotin System (NEN Life Science Products). Serial sections were stained with a rabbit polyclonal antibody to AFP (Dako, A008) at a dilution of 1/400. Endogenous peroxidase was blocked with aqueous hydrogen peroxide, and antibody binding was detected with the Ultra HRP system (ID Labs).

Sandwich ELISA: 96 well ELISA plates were covered with 0.5 μg of anti-GPC3 Mab 1G12 in 50 μl of PBS per well. The plates were blocked for 2 h with 1% BSA in PBS, and 50 μl of diluted serum samples (1:3 in PBS) were added and incubated overnight at 4° C. After washing the unbound material with 0.1% BSA in PBS, bound GPC3 was detected using an anti-GPC3 sheep polyclonal antibody[22], followed by an incubation with horseradish peroxidase-conjugated donkey anti sheep IgG (Sigma) using O-phenylenediamine (Sigma) and hydrogen peroxide as substrates. In order to quantify the GPC3 present in the serum, a calibration curve of purified GPC3 added to the same dilution of a pool of normal serum was performed in parallel. To determine the presence of GPC3 in normal serum, the GPC3 calibration curve was done in PBS. Each sample was measured three times by quadruplicates.

Statistical analysis: Significance of differences between the groups was determined by Mann-Whitney test.

Serological concentration of AFP: AFP levels in parallel serum samples were determined by a commercially available ELISA kit (Axsym, Abboft).

Example 1

Production and Characterization of Polyclonal Antibodies to GPC3

A portion of the cloned GPC3 cDNA (Filmus et al., supra) encoding the 70 consecutive C-terminal amino acids of human GPC3 was expressed as a glutathione-S-transferase fusion protein in a conventional *E coli* expression system.

The fusion protein, purified on a glutathione column, was used to immunise sheep, using a standard protocol. The polyclonal antibodies were affinity purified against the 70 amino acid immunogen, by conventional methods, as described in "Antibodies, a Laboratory Manual", (1988), Ed. Harlow et al., Cold Spring Harbor. The polyclonal antibodies were used for Western blot and immunoprecipitation studies.

Example 2

Production of Hybridomas Yielding Monoclonal Antibodies to GPC3

The same immunogen, a GST-fusion protein including the C-terminal 70 amino acids of human GPC3, was used to raise monoclonal antibodies. This 70 amino acid region is the least conserved across species and was therefore used to generate antibodies specific for human GPC3. Hybridomas were generated using methods known to those skilled in the art, for example as described in Kohler and Milstein, Nature, 256: 495-497, (1975).

Briefly, Balb/C female mice were immunized with a single i.p. injection containing 50 µg of a His-tagged carboxyl-terminal 70 amino acid human GPC3 fragment emulsified with Titermax Gold™ (Cedarlane) adjuvant. After 21 days, the mice were boosted with 50 µg of the same immunogen in the absence of adjuvant. Two days later, blood samples were collected from the tail vein, and the mouse sera obtained. The anti-GPC3 titre in the sera samples was tested by an enzyme-linked immunosorbent assay (ELISA) using as negative control the pre-immunized serum from the same mice. Splenocytes obtained from the two mice with highest titre were fused with SP2/0 Ag14 mouse myeloma cells (relation 6:1) with polyethylene glycol 4000 using standard procedures[1] (Parkin, D. M., Pisani, P. & Ferlay, J., Global cancer statistics. C A. *Cancer J. Clin.*, 49, 33-64, 1, (1999). The fused cells were plated into 96-well plates in α-MEM, 10 mM Hepes, 50 µM 2-mercaptoethanol, 20% FBS supplemented with Nutridoma-CS™ (Roche) as source of growth factors and hypoxanthine, aminopterin and thymidine to select the hybrids. The clones obtained were screened by ELISA, using 96-well plates loaded with 0.05 µg of carboxyl-terminal GPC3 fragment/well. The plates were blocked for 2 hours with 1% bovine serum albumin (BSA) in phosphate-buffered saline (PBS), and incubated with the conditioned culture supernatants. Binding of the first antibody was detected using horseradish peroxidase-conjugated goat anti-mouse-IgG and goat anti-mouse-IgM (StressGen™) with O-phenylenediamine and hydrogen peroxide as substrates. The positive clones were rescreened by immunofluorescence using GPC3-transfected cells. The selected hybridomas (1G12 and 8H5) were cloned twice, their isotype determined (IgG1, K) using Isostrip™ (Roche) and they were purified from conditioned culture supernatants using protein A column chromatography Affi-Gel Protein A MAPS II kit, (Bio-Rad™).

Antibodies produced by the hybridomas were screened against the 70 amino acid GPC3 fragment using an ELISA. Positive clones were then tested for their capacity to stain specifically GPC3-transfected cells. Two hybridomas (1G12 and 8H5) produced antibodies that showed strong and specific immunostaining of GPC3-transfected cells. FIG. 1 illustrates staining of 293 cells with 1G12 antibodies, followed by a fluorescent second antibody. Panels A and C are phase contrast micrographs and panels B and D are fluorescent micrographs. Panels A and B show 293 cells transfected with the vector alone, while panels C and D show cells transfected with the GPC3-containing vector. In this example, the cells were stained in the presence of 10 µg/ml of monoclonal antibody (mAb) 1G12. Panel D clearly demonstrates specific staining with mAb 1G12. No staining is seen in the cells transfected with the vector alone (panel B).

Example 3

Characterization of Monoclonal Antibodies

Figure 2:
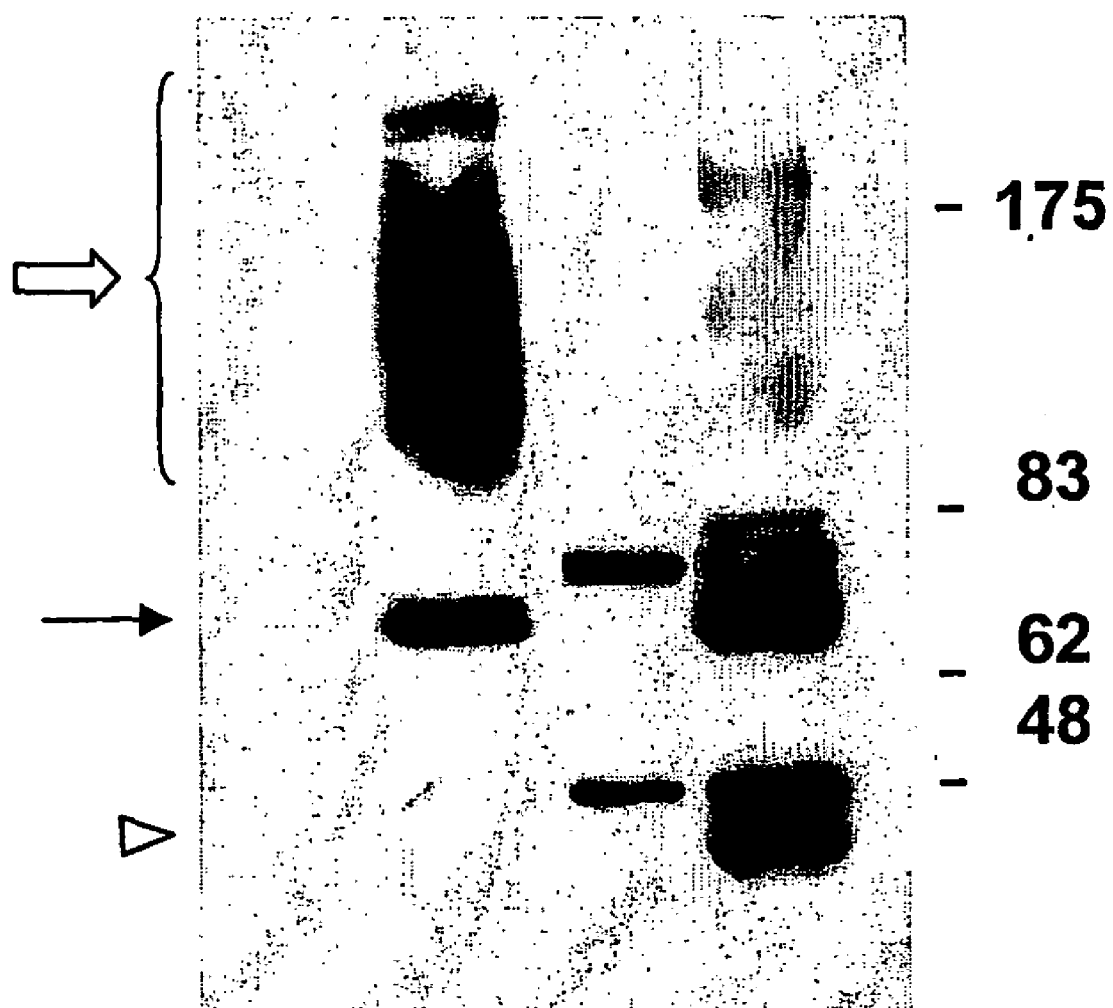
FIG. 2 shows a Western blot (WB) analysis of proteins from 293 cells transfected with vector alone (EF) or HA-tagged GPC3 (GPC3). Membranes were incubated with anti-GPC3 antibody 1G12 or anti-HA antibody (12CA5). Solid arrow: GPC3 core protein; open arrow: glycanated forms of GPC3; arrowhead: a cleavage product containing N-terminus of GPC3 which does not contain epitope detected by 1G12. Numbers on right correspond to molecular weight markers.

The specificity of the two monoclonal antibodies produced by 1G12 and 8H5 hybridomas was confirmed by Western blot analysis of protein lysates from HA-tagged-GPC3-transfected cells. As shown in FIG. 2, antibody 1G12 detected the band corresponding to the GPC3 core protein, and the smear corresponding to the glycanated form of GPC3. As a control, a parallel Western blot was run with an anti-HA antibody (12CA5).

Example 4

GPC3 in Tissue Sections

Paraffin sections of HCC tumour and surrounding non-malignant cells were immunohistochemically stained with anti-GPC3 monoclonal antibody 1G12 as described above. The anti-GPC3 antibody was detected using a biotinylated anti-mouse immunoglobulin second antibody and the bound second antibody was detected using streptavidin conjugated to horse radish peroxide.

Figure 3:
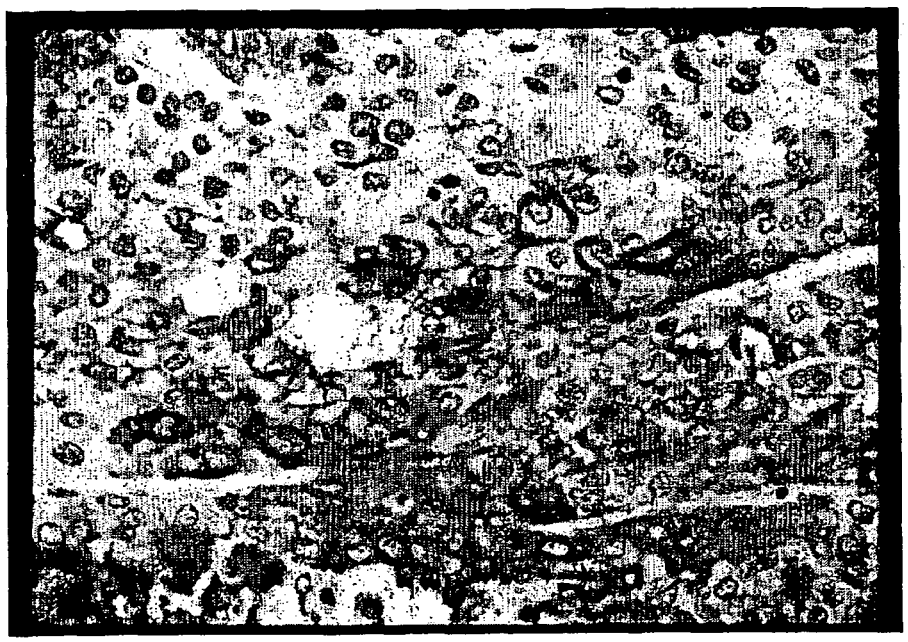
FIG. 3 shows photomicrographs of immunohistochemically stained sections of hepatocellular carcinoma using monoclonal antibody 1G12. Panel A: 16X overview of highly GPC3-positive HCC (T) surrounded by non-stained non-tumour liver tissue (N); Panel B: 400× view of same tissue showing cytoplasmic granules and membrane staining.
Figure 3:

FIG. 3 shows that the anti-GPC3 monoclonal antibody, 1G12, bound strongly to tumour cells, but did not bind at all with the normal hepatocytes. In addition to the predicted presence of GPC3 on the cell membrane, significant staining in the cytoplasm was also seen. The cytoplasmic staining was mostly granular and close to the cell surface. Occasionally perinuclear staining was observed. Non-parenchymal cells were generally negative, with the exception of macrophages. These results indicate that anti-GPC3 monoclonal antibodies can be used to diagnose HCC in liver tissue sections by detection of GPC3.

Example 5

In Vitro Determination of GPC3 Expression in Malignant and Benign Lesions

Table 1 summarizes the results of an immunohistochemical study of monoclonal antibodies to GPC3 reacting with fifteen different hepatocellular carcinomas. Twelve (80%) of these HCC's reacted with the monoclonal antibodies to GPC3. There was some variation in the number of stained cells that reacted with the anti-GPC3 mAb in each tumor. Positive cells were usually clustered into clone-like regions. In all cases, the non-malignant liver cells surrounding the tumor were negative.

TABLE 1

GPC3 expression in HCC.

| Acc. No. of HCC's | mAb 1G12 | mAb 8H5 | % of positive cells |
|---|---|---|---|
| 2188-96 I | 3 | 3 | 70 |
| 21914- | 3 | 3 | 80 |
| 4865-99 | 3 | 3 | 90 |
| 7530-93 A | 3 | 3 | 100 |
| 7590-98 B | 3 | 2 | 90 |
| 28828-99 A | 3 | — | 100 |
| 12056-97 | 2 | 2 | 40-60 |
| 19626-98 A | 1 | 1 | 1-5 |
| 18891-96 | 1 | 1 | 5 |
| 6301-99 B | 1 | 1 | 20 |
| 2978-97 B | 1 | 1 | 1 |
| 5940-96 | 1 | 1 | 5-10 |
| 21424-98 A | 0 | 0 | — |
| 10355-97 D | 0 | 0 | — |
| 10865-01 C | 0 | 0 | — |

Table 2 shows a summary of the results of reactions of an anti-GPC3 monoclonal antibody with malignant and non-malignant liver tissues. 6 liver adenomas and 9 liver dysplasias were negative for GPC3.

TABLE 2

GPC3 expression in non-malignant liver tissues

| Type of Liver Tissue | Number of tissue types tested | GPC3 expression (%) |
|---|---|---|
| HCC | 23 | 19 (83%) |
| High-grade dysplasia | 3 | 0 (0%) |
| Low-grade dysplasia | 6 | 0 (0%) |
| Hepatocellular adenoma | 6 | 0 (0%) |
| Normal liver | 34 | 0 (0%) |

The data indicate that GPC3 is not expressed in normal liver and in benign lesions, while the majority of HCCs express detectable levels of glypican-3.

Example 6

Immunological Assay for GPC3 Detection

Figure 4:
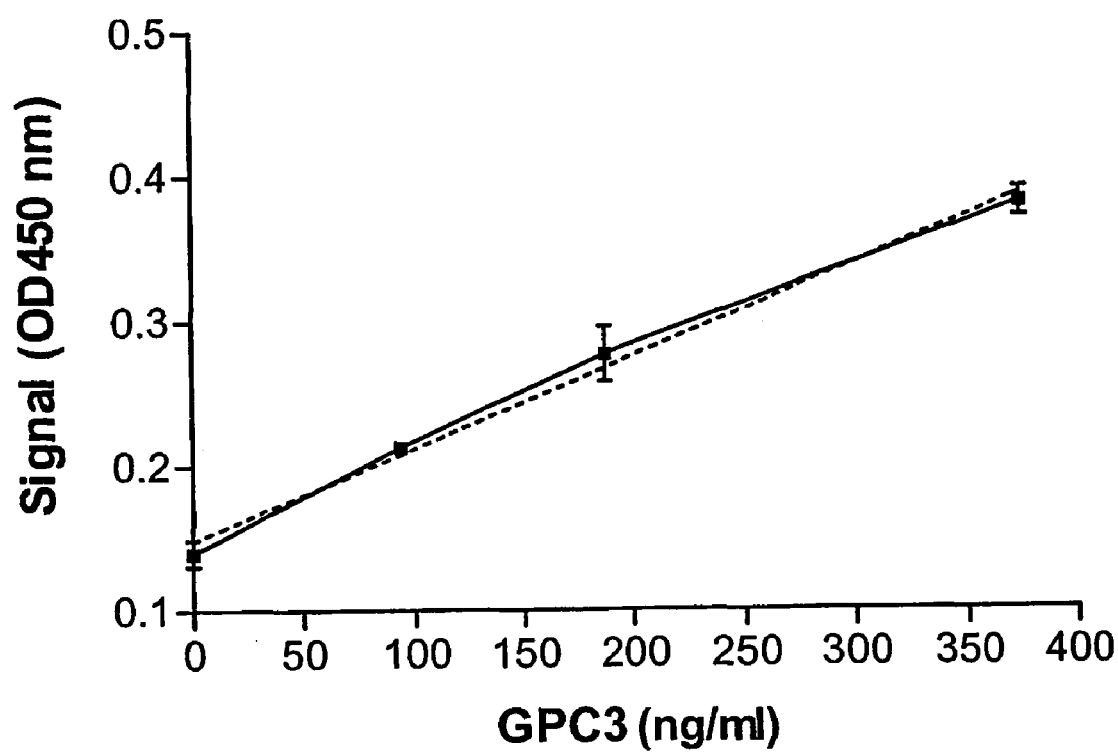
FIG. 4 shows the relationship between GPC3 concentration and optical density in an ELISA assay for GPC3.

A sandwich ELISA was used to determine GPC3 in the serum of patients diagnosed with HCC. For the ELISA, 96-well plates were coated with anti-GPC3 monoclonal antibody 1G12, and an aliquot of test serum was added. Unbound material was removed by washing, and bound GPC3 was detected using anti-GPC3 sheep polyclonal antibodies prepared as in Example 1, complexed directly or indirectly to a detection reagent useful for detecting the presence of the immune complex. The optical density of the sample was measured and compared to results of a standard curve. FIG. 4 illustrates the standard curve for the assay. Assay results were linear within the tested range.

A protocol was established to collect sera from patients who were being treated for HCC at the Toronto General Hospital, and whose written consent was obtained. In a preliminary study, sera were collected from 9 patients with established HCC. Normal sera were also collected from 38 blood donors and pooled. GPC3 levels were determined by a sandwich ELISA assay, using 1:3 (serum:PBS) dilution of the sample. Each sample was analyzed in quadruplicate. The concentration of GPC3 was obtained by comparing the OD obtained from each sample with a standard curve generated by adding various amounts of GPC3 to the same dilution of a pool of normal serum.

Table 3 summarizes the results of the study. Five of the nine HCC patients (55%) had GPC3 values that were significantly elevated. None of these patients had significantly increased AFP levels. GPC3 was not detectable in any of the normal samples.

TABLE 3

| Patient # | GPC3 level (ng/ml) | Standard error | P |
|---|---|---|---|
| 1 | 100.6 | 17.7 | 0.0027 (*) |
| 2 | 292.4 | 16.7 | <0.0001 (*) |
| 4 | 84.9 | 19.3 | 0.0081 (*) |
| 5 | 0 | 9.6 | NS |
| 6 | 75.4 | 9.0 | 0.0014 (*) |
| 7 | 14.9 | 3.5 | NS |
| 8 | 44.4 | 54.3 | NS |
| 9 | 102.6 | 12.9 | 0.0001 (*) |
| 10 | 0 | 12.9 | NS |
| Pooled Normal sera | 0 | 10.1 | |

* significantly different than normal serum

Figure 5:
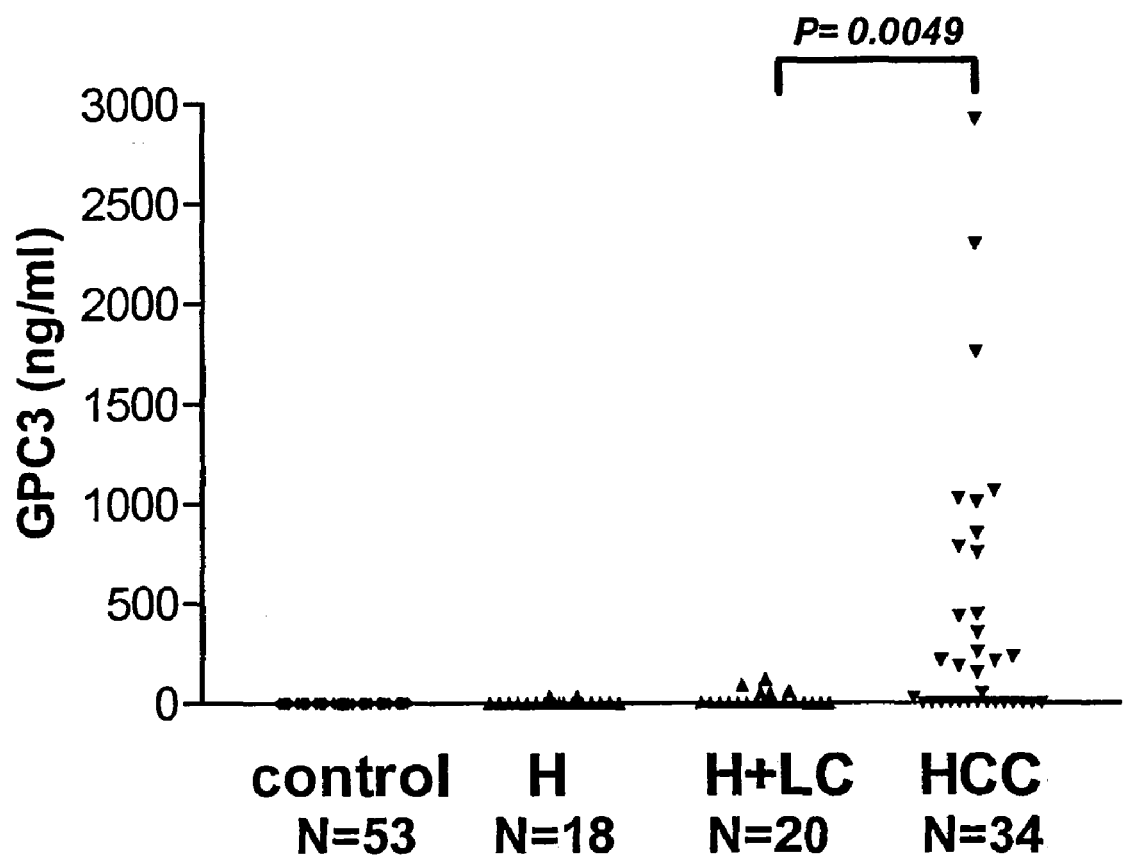
FIG. 5 shows levels of GPC3 in serum from controls, hepatitis patients (H), hepatitis plus cirrhosis patients (H+LC) and hepatocellular carcinoma patients (HCC), determined by ELISA, results shown represent the average of quadruplicates. Significance of difference between the average GPC3 values for the HCC patients and cirrhotic patients is shown at the top of the figure.

Additional studies were conducted using a sandwich ELISA to measure the levels of serum GPC3 in 53 healthy individuals, 18 patients with hepatitis, 20 with hepatitis plus cirrhosis, and 34 with HCC. It was found that GPC3 was undetectable in all healthy individuals and that 18 out of 34 HCC patients (53% sensitivity) had significantly elevated levels of serum GPC3, with values ranging from 151 to 2924 ng/ml (FIG. 5 and Table 4). In addition, GPC3 was undetectable in all patients with hepatitis and it was detected in only 1 of 20 (5%) patients with hepatitis plus cirrhosis, at a level of 117 ng/ml (95% specificity). Statistical analysis using the Mann-Whitney test showed that the average serum levels (ng/ml) of GPC3 in patients with HCC is significantly higher than those with hepatitis plus cirrhosis, hepatitis and healthy donors and there was no significant difference among the last three groups.

Example 7

Comparison of GPC3 and AFP Levels

Serum AFP levels were measured in the same set of 34 HCC patients described in Example 6, using a commercially available ELISA (Axsym, Abbott). Table 4 shows a comparison of the AFP and GPC3 values obtained.

TABLE 4

Serum concentration of GPC3 and AFP in patients with HCC

| Patient # | GPC3 (ng/ml) | AFP (ng/ml) | Etiology |
|---|---|---|---|
| 1 | 2924 | 133 | HBV |
| 2 | 2295 | 12 | HCV |
| 3 | 1758 | <5 | HBV |
| 4 | 1065 | 34 | HCV |
| 5 | 1026 | 14 | HCV |
| 6 | 1006 | 30 | HBV |
| 7 | 849 | 14 | HCV |
| 8 | 783 | 23 | HBV & HCV |
| 9 | 755 | <5 | HBV |
| 10 | 445 | 14428 | Unknown |
| 11 | 433 | 10 | HBV |
| 12 | 351 | 7809 | HCV |
| 13 | 252 | 8629 | HCV |
| 14 | 235 | 1628 | HCV |
| 15 | 214 | 78 | Alcoholic |
| 16 | 211 | <5 | Alcoholic |
| 17 | 184 | 5 | HBV |
| 18 | 151 | 40 | Alcoholic |
| 19 | 47 | 52000 | Alcoholic |
| 20 | 26 | 1516 | HCV |
| 21 | 0 | 8 | HBV |
| 22 | 0 | 30 | HBV |
| 23 | 0 | <5 | HBV |
| 24 | 0 | 15 | HBV |
| 25 | 0 | <5 | HBV |
| 26 | 0 | 488 | Unknown |
| 27 | 0 | 5 | Alcoholic |
| 28 | 0 | 2603 | Unknown |
| 29 | 0 | 194 | HBV |
| 30 | 0 | 13 | HBV, HIV |
| 31 | 0 | 67 | HCV |
| 32 | 0 | 27 | HBV |
| 33 | 0 | 74 | HCV |
| 34 | 0 | 1900 | HCV |

The present invention is not limited to the features of the embodiments described herein, but includes all variations and modifications within the scope of the claims.

We claim:

1. A method for screening a subject for hepatocellular carcinoma (HCC), comprising:
obtaining a body fluid sample from the subject;
determining the level of glypican-3 (GPC3) in the sample; and detecting the presence of a detectable level of expressed GPC3 protein in the sample, this level being indicative of HCC in the subject.

2. The method of claim 1 wherein the GPC3 level of the sample is determined by an immunological method.

3. The method of claim 2 wherein the method employs an antibody or antibody fragment which binds specifically to human GPC3 or to a fragment thereof.

4. The method of claim 3 wherein the antibody or fragment binds specifically to an epitope within the 70 consecutive carboxy-terminal amino acids of human GPC3.

5. The method of claim 3 wherein the antibody is a polyclonal antibody.

6. The method of claim 3 wherein the antibody is a monoclonal antibody.

7. The method of claim 3 wherein the fragment is selected from the group consisting of Fab, F(ab')2 and Fv.

8. The method of claim 3 wherein the antibody or antibody fragment carries a detectable label.

9. The method of claim 3 wherein the antibody or antibody fragment is detected by using a second antibody which binds specifically to the anti-GPC3 antibody or antibody fragment and comprises a component of a signal-generating system.

10. The method of claim 3 wherein the anti-GPC3 antibody or fragment is attached to a solid substrate, the sample is contacted with the solid substrate to permit GPC3 in the sample to bind to the attached anti-GPC3 antibody or fragment, the solid substrate is washed and the bound GPC3 is determined using a second antibody which binds specifically to the anti-GPC3 antibody or antibody fragment and comprises a component of a signal-generating system.

11. The method of claim 9 wherein the second antibody is conjugated to horse radish peroxidase.

12. The method of claim 1 wherein the body fluid is serum or plasma.

13. The method of claim 1 wherein the subject is a human subject.

14. The method of claim 3 wherein the antibody is a single chain antibody molecule.

15. The method of claim 3 wherein the antibody is an antibody selected from the group consisting of IgG, IgM, IgA, IgE, IgD and any subclass thereof.

16. A method for screening a subject for hepatocellular carcinoma (HCC), comprising:
 obtaining a body fluid sample of serum, plasma, or whole blood from the subject;
 determining the level of glypican-3 (GPC3) in the sample; and
 detecting the presence of a detectable level of expressed GPC3 protein in the sample, this level being indicative of HCC in the subject.

* * * * *